(12) United States Patent
Feige et al.

(10) Patent No.: US 7,320,685 B2
(45) Date of Patent: Jan. 22, 2008

(54) METHOD AND DEVICE FOR IDENTIFYING AN EYE THAT IS TO BE TREATED IN OPERATIONS

(75) Inventors: Torsten Feige, Jena (DE); Holger Maeusezahl, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 527 days.

(21) Appl. No.: 10/399,440

(22) PCT Filed: Oct. 22, 2001

(86) PCT No.: PCT/EP01/12171

§ 371 (c)(1),
(2), (4) Date: Apr. 17, 2003

(87) PCT Pub. No.: WO02/32351

PCT Pub. Date: Apr. 25, 2002

(65) Prior Publication Data

US 2004/0020983 A1 Feb. 5, 2004

(30) Foreign Application Priority Data

Oct. 20, 2000 (DE) .............................. 100 52 201

(51) Int. Cl.
*A61F 9/01* (2006.01)
(52) U.S. Cl. .......................................... 606/5; 128/898
(58) Field of Classification Search ................ 128/898; 606/4

See application file for complete search history.

(56) References Cited

U.S. PATENT DOCUMENTS

| | | | | | |
|---|---|---|---|---|---|
| 4,415,802 | A | * | 11/1983 | Long | 235/382 |
| 4,641,349 | A | * | 2/1987 | Flom et al. | 382/117 |
| 4,857,713 | A | * | 8/1989 | Brown | 705/3 |
| 5,049,147 | A | * | 9/1991 | Danon | 606/10 |

(Continued)

FOREIGN PATENT DOCUMENTS

DE 42 32 021 C2 7/1997

(Continued)

OTHER PUBLICATIONS

U.S. Appl. No. 60/206,091, Huppertz et al.

*Primary Examiner*—Henry M. Johnson, III
(74) *Attorney, Agent, or Firm*—Darby & Darby

(57) ABSTRACT

A method for identifying the site of an operation during an operation, in particular using a laser system, with the help of unique data about the operation site. A first copy of the unique data is stored in a laser system, the unique data being located in the vicinity of the operation site and/or directly at said operation site. Before the start of the operation, the first copy and the unique data are compared to verify if they are identical and the result of said verification is forwarded to the laser system. In addition a device for identifying an operation site during an operation includes a laser system having a storage unit for storing data and a reading unit configured to determine unique data about the operation site and to provide a first copy of the unique data to the storage unit. The device also includes a comparator device operably connected to the storage device and configured to compare the first copy and the unique data for identity.

10 Claims, 2 Drawing Sheets

U.S. PATENT DOCUMENTS

| | | | |
|---|---|---|---|
| 5,381,487 A * | 1/1995 | Shamos | 382/115 |
| 5,401,059 A * | 3/1995 | Ferrario | 283/67 |
| 5,425,729 A * | 6/1995 | Ishida et al. | 606/13 |
| 5,572,596 A * | 11/1996 | Wildes et al. | 382/117 |
| 5,715,836 A * | 2/1998 | Kliegis et al. | 600/425 |
| 5,749,361 A | 5/1998 | Mateyko | 128/653.1 |
| 5,891,131 A * | 4/1999 | Rajan et al. | 606/5 |
| 5,901,238 A * | 5/1999 | Matsushita | 382/117 |
| 5,956,122 A * | 9/1999 | Doster | 351/210 |
| 6,005,962 A * | 12/1999 | Hirota et al. | 382/124 |
| 6,028,949 A * | 2/2000 | McKendall | 382/117 |
| 6,069,689 A | 5/2000 | Zeng et al. | 356/73 |
| 6,099,522 A * | 8/2000 | Knopp et al. | 606/10 |
| 6,106,513 A * | 8/2000 | McMillen et al. | 606/4 |
| 6,134,339 A * | 10/2000 | Luo | 382/115 |
| 6,234,900 B1 * | 5/2001 | Cumbers | 463/29 |
| 6,247,813 B1 * | 6/2001 | Kim et al. | 351/206 |
| 6,296,634 B1 * | 10/2001 | McMillen et al. | 606/10 |
| 6,364,873 B1 * | 4/2002 | McMillen et al. | 606/10 |
| 6,402,737 B1 | 6/2002 | Tajima et al. | |
| 6,419,671 B1 * | 7/2002 | Lemberg | 606/5 |
| 6,424,727 B1 * | 7/2002 | Musgrave et al. | 382/117 |
| 6,425,860 B1 * | 7/2002 | Sadkhin | 600/300 |
| 6,439,422 B1 * | 8/2002 | Papp et al. | 221/13 |
| 6,497,358 B1 * | 12/2002 | Walsh | 235/380 |
| 6,519,569 B1 * | 2/2003 | White et al. | 705/3 |
| 6,546,121 B1 * | 4/2003 | Oda | 382/117 |
| 6,585,723 B1 | 7/2003 | Sumiya et al. | |
| 6,591,001 B1 * | 7/2003 | Oda et al. | 382/117 |
| 6,601,729 B1 * | 8/2003 | Papp | 221/25 |
| 6,671,563 B1 * | 12/2003 | Engelson et al. | 700/2 |
| 6,817,998 B2 * | 11/2004 | LaHaye | 606/11 |
| 6,990,588 B1 | 1/2006 | Yasukura et al. | |
| 7,001,018 B1 * | 2/2006 | Martin | 351/211 |
| 2001/0056276 A1 * | 12/2001 | LaHaye | 606/5 |

FOREIGN PATENT DOCUMENTS

| | | |
|---|---|---|
| JP | 11262492 | 9/1999 |
| JP | 11338826 | 12/1999 |
| JP | 2000139996 | 5/2000 |
| JP | 2000166882 | 6/2000 |
| JP | 200510975 | 8/2000 |
| WO | WO-9743453 | 11/1997 |
| WO | 9900690 | 1/1999 |
| WO | WO 01/28476 | 4/2001 |
| WO | WO 01/89373 A2 | 5/2001 |

* cited by examiner

I.

II.

METHOD AND DEVICE FOR IDENTIFYING AN EYE THAT IS TO BE TREATED IN OPERATIONS

BACKGROUND

The present invention relates to a method and a device for identifying an operation site to be treated, in particular an eye, in laser operations.

In laser operations, in particular of an eye, data allowing individual treatment of an eye is required for controlling the laser. This data is usually acquired or determined as patient data; methods such as eyesight testing, refractometer, measuring the topography, for example, of the cornea or of the lens, as well as the aberration of the eye being used for this purpose. This data is stored, whether in a computer-aided manner or manually in a file. Such data includes name, sphere, cylinder, axis, eye (left/right), topography, aberration, etc.

In a later step, this data is entered (sphere, cylinder, axis) or the shot coordinates for the surgical laser are loaded, which were obtained from calculations of topography-aided data or the derivation of coordinates from measurement of the aberrations of the eye. After that, the laser operation is performed based on the data entered.

Thus, the data acquisition and the use of these data sets are separated in space and time. The association between the data and the patient or the individual eye is accomplished using the patient's personal data such as name, first name, date of birth, etc.

Due to the separation in space and time between the acquisition of the data and its use for a laser operation, a connection between the patient's eye at which the data was obtained and the patient's eye on which the operation is to be performed is only given by way of aids. These aids are predominantly the patient's name, the ID number of the physicians' practices, and information on the eye (left or right) from which the data was obtained.

Therefore, this can result in an incorrect association between the data set of the correction and the specific eye under operation. This may be due to the system software used for maintaining the data sets, or else to human failure. In particular, the right and left eyes of the same patient can easily be confused, even when acting in the most careful manner during data acquisition. Confusion of patients with each other (similarity of names, inattentiveness during data acquisition, etc.) is also possible.

An object of the present invention is to provide a method and a device for identifying an operation site, in particular an eye, during a laser operation, which prevent the risk of operations of the wrong operation site or eye.

The present invention provides a method for identifying an operation site during an operation, in particular using a laser system, with the help of unique data about the operation site, a first copy of the unique data being stored in the laser system, the unique data being located in the immediate vicinity of the operation site and/or at the operation site, the first copy and the unique data being checked for their identity before the operation begins, and the result of the identity check being passed on to the laser system. This enables the individual operation site, mainly the eye, to be uniquely identified as the correct one for which the shot positions are provided in the laser. In this way, it is prevented that a patient is treated with incorrect shot data and, thus, that corrections, for example, of his/her eye are made that were calculated for a different patient.

Laser systems are understood to mean surgical systems having a laser, for example, an excimer laser such as a spot scanning excimer laser. Preferably, these laser systems also include computers to carry out the treatment in a computer-aided manner. Particularly preferably, accessory systems such as eye-tracking systems are also provided, as well as lighting devices for the operation site, i.e., especially for the eye.

The unique data is unique with respect to the operation site. Therefore, it is possible for an operation site to be uniquely distinguished from another operation site on the basis of this unique data.

The first copy of the unique data is a copy of the relevant data content that uniquely identifies the eye. This first copy can be stored in the laser system and is thus available to the laser system in the later course of the operation. This unique data is particularly preferably determined prior to the operation and is then available in the further course of the operation.

The unique data is particularly preferably located in the immediate vicinity of the operation site and/or at the operation site. Therefore, it is particularly preferred for this unique data to be immediately next to the eye or even in the eye. The data here can preferably be additionally attached data or data that is already available directly in the operation site or eye. Thus, for example, it is possible for this unique data to be spatially and temporally bound to the eye in a fixed manner, for example, using a sticker, a color marking, preferably as a bar code, a microchip firmly connected to the eyebrow, etc., or the unique data is data that is already located at the operation site, i.e., fixed parameters which uniquely define this operation site, in particular the eye, such as a fingerprint defines a thumb.

Preferably, the first copy of the unique data is then compared to the unique data before the operation begins, thus performing an identity check. Then, the result of this identity check is preferably passed on to the laser system. The further procedure can then be made dependent on the result of this identity check. Thus, for example, it is possible not to permit the operation at all unless the identity check has been completed successfully. Moreover, it is conceivable to inform the operator of a failed identity check before the operation begins.

According to a preferred exemplary embodiment of the present invention, the unique data includes the patient's name, the patient's first name, the patient's data of birth, patient ID, physician ID, information about the operation site, or a combination of individual pieces or all of this data. Thus, for example, it is possible to generate a character string containing information about the specific eye of a specific patient, thus making this eye unique. However, it is particularly preferred to use information about the operation site itself, in particular, vessel patterns and/or patterns of the iris. For this purpose, it is particularly preferred to use vessel patterns of the fundus of the eye, which are different for each eye, even of the same patient, and which have the most individual characteristics uniquely identifying the eye. The pattern of the iris is particularly preferred as well. These patterns are unique as well as stable in time and space. This information about the eye has the further advantage that many laser systems already contain measuring devices with possibilities to record images as well as image-processing components (topography devices, aberrometers, etc.). Thus, the characteristic or the unique data can be determined and stored with the data set particularly preferably concurrently with the data acquisition. On the side of the operation device, image-processing systems (eye-tracking systems)

are frequently used as well. Using these systems, it is now possible for the characteristic or the unique data to be determined from the eye currently present for the operation and to be compared to the characteristic in the data set. If the characteristic is identical, then the unique association is given.

In particularly preferred exemplary embodiments of the present invention, the unique data is embodied as a bar code, microchip, character strings, or a combination of these types of representation. This unique data, which is then preferably arranged in the immediate vicinity of the operation site can, for example, be stuck, drawn, applied, or painted on.

Moreover, the present invention is achieved by a device for identifying an operation site during an operation, particularly preferably for carrying out one of the methods according to the present invention, containing a laser system having a storage unit with a storage of unique data about the operation site and a laser unit, the unique data being determinable using the laser unit, a first copy of the unique data being storable in the storage unit, and provision being made for a comparator device which allows the first copy and the unique data to be checked for their identity. Using such a device, it is possible both to acquire unique data using a laser unit, such as a bar code laser or an image sensing unit, and to store this unique data in the form of a copy in the storage unit so that it can later be checked with the unique data using a comparator device.

This device guarantees that the obtained data is always uniquely associated with the eye from which it was obtained.

Confusion of names, etc., no longer matter because, primarily, the data is always linked to eye and not to the name. Moreover, these solutions can preferably be used actively or passively.

In the case of passive use, the data set is selected as before using patient names, etc.; immediately thereafter, the laser unit or an identification unit looks for the characteristic or the unique data at the eye and compares it to the data set. In case of discrepancy between the characteristics, operation is not permitted.

In the case of active use, the patient's eye is examined directly using the laser unit or the identification unit, and the matching data set is automatically loaded into the laser. Preferably, this patient data (such as name, etc.) is then also indicated to the physician.

Moreover, it is possible to use the present invention such that it includes attachment of the unique data or of this additional characteristic, or to obtain this unique data directly from the eye itself.

It is particularly preferred to recheck the eye correction state shortly before the operation. In this manner, it is in addition possible to prevent double operations of the same eye.

BRIEF DESCRIPTION OF THE DRAWING

In the following, advantageous refinements of the present invention are described with reference to drawings, in which

FIG. 4 shows a flow chart of the method according to the present invention.

DETAILED DESCRIPTION

Figure 1A:
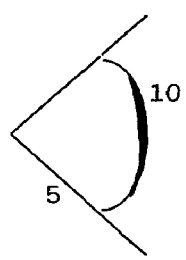
FIG. 1 is a schematic representation of an exemplary embodiment of the method according to the present invention.
Figure 1A:
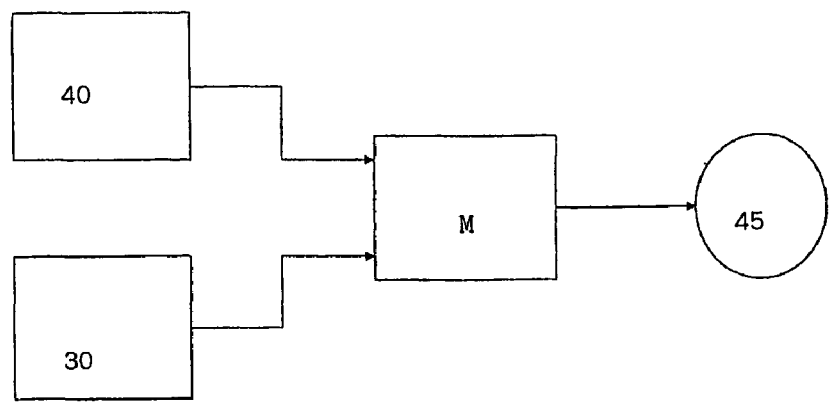
Figure 1B:
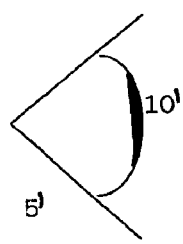
Figure 1B:
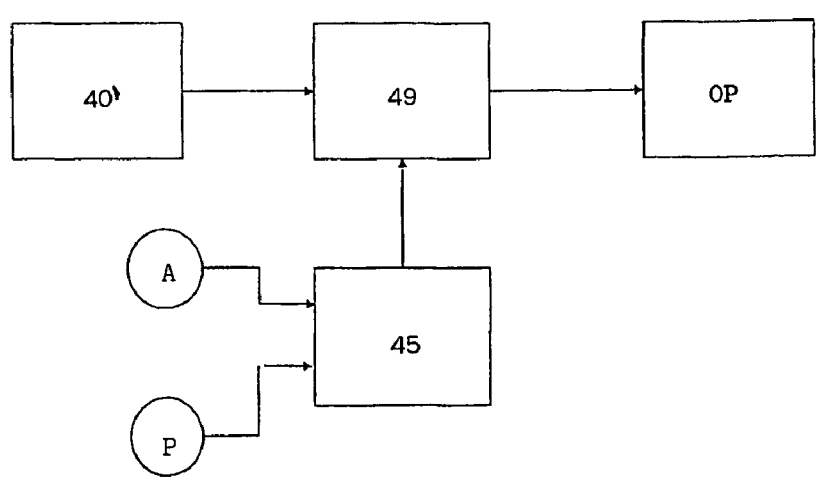

FIG. 1 a schematic representation of an exemplary embodiment of the method according to the present invention in which, in a first step I, an eye 5 having a representative unique characteristic 10 is scanned using a reading or identification unit 40, determining the unique data 10 or the characteristic, here, for example, the pattern of the iris. Using a shot data acquisition unit 30, the existing defects of eye 5 or the intended basis for the shot data for correcting eye are determined as a data set. These two results are combined in a mixer stage M so that the unique data or the characteristic is added to the shot data set. Furthermore, it is possible to include the acquisition of patient data, which can also be added to the data set using a further input unit (not shown). This complete data set is then stored in storage device 45.

Later, in a second step II, the specific eye 5' which is present for the operation and has the unique characteristic 10' of the iris pattern is scanned, and unique characteristic 10' is determined in identification unit 40'. In storage device 45, the shot data appropriate for the characteristic is then either loaded into storage unit 45 on the basis of the previously stored shot data and/or this data is transferred to storage unit 45 through direct entry of the data, such as sphere, aberration, etc., by the physician. Then, characteristic 10' determined from the specific eye 5' located in front of the laser and characteristic 10, which is available in storage device 45 and which was previously determined for the present shot data set in step I are compared in comparator device 49. If the two characteristics 10 and 10' match, comparator device 49 outputs a signal enabling operation OP.

FIG. 4 shows a flow chart illustrating steps of a method for identifying an eye that is to be treated during an operation. In a first method step, unique data about the operation site is identified, the unique data being located in an immediate vicinity of the operation site, wherein the operation site is an eye. See block 100. In a second step, a first copy of the unique data is stored in the laser system. See block 120. In a third step, an identity check is performed between the first copy and the unique data so as to create a result. See block 140. In a fourth step, the result is provided to the laser system before the operation begins. See block 160.

In this manner, the association with the shot data present for the operation is verified on the basis of the unique data or characteristic 10' present in or at eye 5', thus providing exceptional safety from confusions or misassociations during the subsequent operation.

Figure 2:
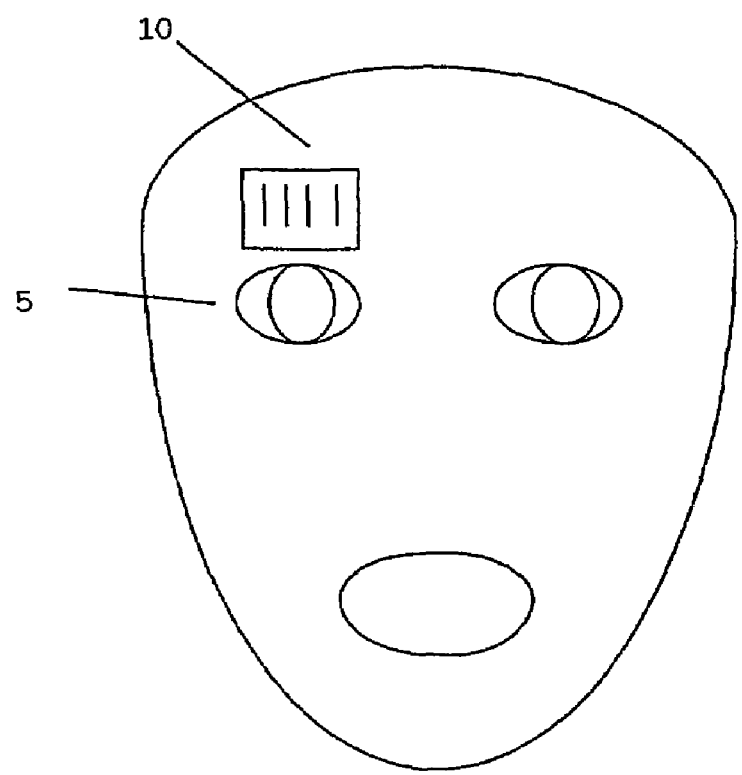
FIG. 2 shows an exemplary embodiment for attachment of the unique data near the eye.

FIG. 2 shows an exemplary embodiment for attachment of the unique data near the eye. In this context, unique characteristic 10 is firmly attached, preferably glued on, as a bar code above eye 5 at the height of the eyebrow. In this manner, the unique characteristic or unique data 10 embodied in the bar code can be determined both during the acquisition of the correction data in step I as well as during the checking in step II.

Figure 3:
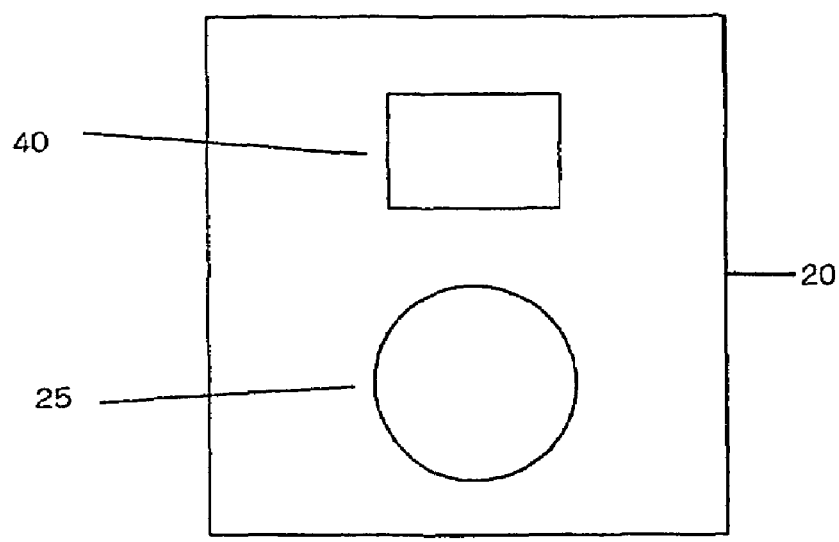
FIG. 3 is a schematic representation of an exemplary embodiment of the present invention as a data acquisition or treatment device.

FIG. 3 is a schematic representation of an exemplary embodiment of the present invention as a data acquisition or treatment device. In this context, besides surgical beam unit 25, from which the scanning beam for determining the correction data in step I and the laser beam with which the operation is performed in step II, provision is made for a reading unit or identification unit 40 which allows determination of unique characteristic 10. It is particularly preferred for this reading unit 40 to be implemented by devices in laser system 20 that are present in conventional laser systems anyway, such as topography devices and aberrometers in step I or eye trackers in step II.

What is claimed is:

1. A method for identifying an operation site during an operation using a laser system, the method comprising:
   identifying unique data about the operation site, the unique data being located in an immediate vicinity of the operation site, wherein the operation site is an eye;
   performing an identity check between the unique data and a previously stored copy of unique data so as to create a result of the identity check; and
   providing the result to the laser system before the operation begins.

2. The method as recited in claim 1, wherein the unique data is located at the operation site.

3. The method as recited in claim 1, wherein the unique data includes at least one of a patient name, a patient first name, a patient date of birth, a patient ID, a physician ID, and information about the operation site.

4. The method as recited in claim 3, wherein the information about the operation site includes a pattern.

5. The method as recited in claim 4, wherein the pattern includes at least one of a vessel pattern and an iris pattern.

6. The method as recited in claim 1, wherein the unique data is embodied as at least one of a bar code, a microchip, and a character string.

7. The method as recited in claim 1, further comprising beginning the operation using the laser system when the result is positive.

8. A device for identifying an operation site for an operation, the device comprising:
   a reading unit configured to perform a first scan of a first eye in the operation site prior to the operation to determine a first representative unique characteristic of the first eye as a first characteristic data set, wherein the reading unit is configured to perform a second scan of a patient eye subsequent to the first scan and prior to the operation to determine a second representative unique characteristic of the patient eye as a second characteristic data set;
   a shot data acquisition unit configured to determine shot data for correcting a defect of the first eye;
   a mixer stage in operative connection with the reading unit and configured to add the first characteristic data set to the shot data so as to form a complete data set;
   a storage device in operative connection with the mixer stage and configured to store the complete data;
   a comparator device in operative connection to the storage device and the reading unit and configured to compare the first characteristic data set to the second characteristic data set to determine whether identity exists between the patient eye and the first eye;
   a laser device in operative connection with the comparator device and configured to perform the operation, wherein the comparator device enables the laser device to perform the operation only when the identity exists.

9. The device as recited in claim 8, wherein the first and second representative unique characteristics of the eye include a pattern of the eye.

10. The device as recited in claim 9, wherein the pattern includes at least one of a vessel pattern and an iris pattern.

* * * * *